(12) United States Patent
Pine (10) Patent No.: US 8,287,505 B2
(45) Date of Patent: Oct. 16, 2012

(54) OPHTHALMIC DROP DISPENSING TIP ASSEMBLY

(76) Inventor: Jerrold Scott Pine, Boca Raton, FL (US)

( * ) Notice: Subject to any disclaimer, the term of this patent is extended or adjusted under 35 U.S.C. 154(b) by 286 days.

(21) Appl. No.: 12/710,891

(22) Filed: Feb. 23, 2010

(65) Prior Publication Data
US 2010/0211027 A1   Aug. 19, 2010

Related U.S. Application Data

(63) Continuation of application No. 11/463,094, filed on Aug. 8, 2006, now abandoned.

(51) Int. Cl.
*A61M 35/00* (2006.01)
*B65D 37/00* (2006.01)
*B65D 47/18* (2006.01)

(52) U.S. Cl. ........ 604/300; 604/294; 604/295; 604/298; 222/1; 222/215; 222/420; 222/421

(58) Field of Classification Search .................. 604/295, 604/294, 298, 300; 222/1, 215, 420, 421
See application file for complete search history.

(56) References Cited

U.S. PATENT DOCUMENTS

| | | | |
|---|---|---|---|
| 4,909,801 A | 3/1990 | Casey | |
| 5,366,448 A | 11/1994 | Basilice | |
| 5,373,964 A | 12/1994 | Moore | |
| 5,558,653 A * | 9/1996 | Lindstrom | 604/295 |
| 5,584,823 A | 12/1996 | Valberg | |
| 5,932,206 A * | 8/1999 | Pine et al. | 424/78.04 |
| 6,223,947 B1 * | 5/2001 | Bernard | 222/113 |
| 6,508,793 B1 * | 1/2003 | Harrold | 604/302 |
| 7,008,979 B2 * | 3/2006 | Schottman et al. | 523/334 |
| 2002/0055007 A1 * | 5/2002 | Soane et al. | 428/520 |
| 2004/0050881 A1 * | 3/2004 | Deussen | 222/420 |
| 2004/0267214 A1 * | 12/2004 | Kerssies | 604/299 |
| 2005/0054992 A1 * | 3/2005 | Madritsch et al. | 604/294 |
| 2005/0159715 A1 * | 7/2005 | Kusu | 604/295 |
| 2006/0129113 A1 * | 6/2006 | Merrick | 604/294 |
| 2006/0282049 A1 * | 12/2006 | Lee | 604/300 |

* cited by examiner

*Primary Examiner* — Tatyana Zalukaeva
*Assistant Examiner* — Adam Marcetich (57) ABSTRACT

A dispensing tip apparatus for an eye drop dispenser to administer topical ophthalmic solutions is described. The apparatus integrates an ophthalmic solution-dispensing tip with an optical gauging assembly. The tip provides continuous visual feedback about it orientation and relationship to the eye. The dispensing tip when attached to any standard topical ophthalmic solution dispensing bottle or reservoir enables the user to view a target, visually align the dispenser tip, and administer an eye drop with precision. There is also a visual feedback by which the dispenser tip is prevented from gaining too close proximity and contacting the eye, thus preventing contamination of the medication and its dispenser. The visual feedback can also contain textual or graphic information that serves as a promotional advertisement. The is assembly can be attached to the neck of an eye drop bottle or attached to the tip of an eye drop bottle.

20 Claims, 9 Drawing Sheets

Dispensing Instructions

Open Eye Wide and Tilt your head back as far as you can.

Hold VERTICAL above EYE

Look into dispenser, Slowly move it very close until you see a GREEN RING See a PERFECT GREEN RING, Stop, Dispense ONE drop.
SEE RED, You are too close, Back Up.

---

If the Dropper Appears:

| CORRECT DISPENSE | Too Far Move In | Too Close ! Back up | Not Vertical Start Again |

If you see only part of a green circle, the dispenser is not held Vertically – Start again.
Do not touch the surface of the lens, or remove the lens from the tip. Clean only with a dry, lint free cloth.

Figure 12

OPHTHALMIC DROP DISPENSING TIP ASSEMBLY

The present application is a continuation and claims the priority benefit of U.S. patent application Ser. No. 11/463,094 filed Aug. 8, 2006

BACKGROUND OF THE INVENTION

According to clinical studies a staggering 37.6% of all self-administered eye drops miss the eye. One way to improve delivery of eye drops is by providing a visual feedback means so that a person dispensing drops can position an eye drop dispenser at an optimal distance and orientation above the eye. To accomplish visual feedback, the eyedropper needs to incorporate features used in other visual range and orientation devices. One such device is a common range finder used by golfers to gauge their distance from the ball to the hole. In golf range finders, the golfer stands near their ball and looks through a lens directly at the flag on its pole. The flags are uniform at a fixed height above the ground. The closer a golfer is to the flag, the larger it appears in the range finder. The range finder has calibrated hash marks within that correspond to a given distance. The golfer by aligning the appropriate hash mark with the image of the flagpole gets distance feedback. It will be appreciated that if the flagpole were replaced by a circular target, feedback of both distance and horizontal/vertical orientation can be visualized. With some optics engineering this mechanism can be used to gauge distance and orientation between a dispensing tip and the eye.

For years, the primary method of medically treating disorders of the eye has been via topical administration of various medications and other chemical compounds useful in combating a host of ophthalmic ailments. In fact, studies show that when measuring concentrations of these compounds at the desired target site (whether it be in the tear film, intracorneal, or intraocular), topical delivery equals or exceeds those concentrations obtained by systemic routes (oral or intravenous), and has far fewer systemic untoward signs and symptoms (side effects). Thus, it is no wonder that most remedies and medications are delivered via the topical route. Historically, this has been achieved via ointments, suspensions, solutions, contact lenses, collagen shields, and palpebral inserts. Far and away, the most common mode of delivery has been via topical suspensions and solutions. Typically, dispensers have fairly standard sizes and shapes (although there is some slight variation), and there is a reproducible standard drop size that is governed by the dropper (dispenser) tip. As simple as topical delivery may seem to achieve, there are various difficulties and shortcomings with current topical dispensing units (vials and bottles), many of which have not been previously or adequately addressed and solved.

The most common problem that the typical patient experiences when attempting to use an eye drop is the inability to introduce a drop into the eye, or simply missing the eye. There are several reasons for this. First, the normal bottle tip is not clearly visible as it approaches a normal emmetropic, hyperopic, or even myopic eye. This immediately leads to the probability that the first drop will become the "test drop", landing on the cheek, forehead, or eyelashes, leading to waste and frustration. Second, there is a natural aversion to closely approaching objects, causing the eye to wander or drift, and look everywhere but at the dispenser tip. Again, this leads to the possibility that a drop will miss. Finally, most users are not taught how to use eye drops. They are simply given the bottle and instructed to "place one drop in the eye".

The next important issue is one of waste. When a typical eye drop is introduced into the eye, the average inferior cul-de-sac only holds one-quarter to one-half of a standard drop. The remainder is either washed out down the cheek, or drained by the lachrymal system. Large strides in preventing waste were made when a dispenser tip was developed that delivered smaller drop sizes, thus eliminating a portion of waste. However, this advantage is negated if it takes several drops to gain access to the ocular surface. This issue is critical when evaluating cost to the patient and the healthcare system. The cost problem for the patient is obvious: the more drops they use, the greater the amount of money spent. With respect to the healthcare system as a whole, cutting costs are of paramount importance. In fact, many Health Maintenance Organizations (HMO's) will not let their members get refills on their ophthalmic medications more than once a month. The rationale behind this is simple. If the bottle has "x" number of drops in it, it should last "y" number of days. If the patient is not proficient with a high success ratio, then the drops will run out before the specified time allowed. This, in turn, leads to the patient either being without their valuable medications, or having to pay for the medications themselves.

Finally, there is the problem of contamination of the dispenser tip, and cross-contamination between patients. Since the tip is not clearly visible upon the approach to the ocular surface, it oftentimes will inadvertently come in contact with the eye or lid structures. This will lead to an inoculation of the tip with ocular flora, and be a potential source for spreading infection. Although sharing medications in general, especially eye drops, is always discouraged, many different people, whether friends or family members, often find the ease and convenience of sharing overwhelmingly tempting. Again, this can lead to cross-contamination and, in turn, the spread of infection.

Most of the current problems of efficiently dispensing ophthalmic drugs stem from user error. Therefore, it is the goal of this device to create a "user friendly" ophthalmic drug dispenser.

SUMMARY OF THE INVENTION

This invention seeks to create an integrated dispensing tip and optical gauging means for administering topical ophthalmic drug preparations, which enables the patient to direct an eye drop into the eye with the ease and accuracy, previously only attained by a proficient few. In addition, this particular device may serve to prevent cross-contamination, and ultimately save both the patient and the healthcare system money typically lost to waste.

More specifically, this invention relates to a dropper tip with an integrated lens and target system which, when coupled with or integral to any standard topical ophthalmic drug dispensing bottle, enables the user to view the target, align the dispenser tip, and administer an eye drop with precision not attained before. To achieve this precision, the target and lens system is calibrated to align the dispensing tip with the optical axis of the eye at a specified distance from the eye. The resulting geometric relationship between the dispensing tip and the eye insures that a dispensed drop will enter the eye. Prior art such as U.S. Pat. No. 5,558,653 "Targeted eye drop dispenser" which uses visual feedback to align an ophthalmic drug dispenser simply helps place the nozzle along the axis of the eye at an arbitrary distance selected at random by the user. This is only effective if the axis of the eye and the path a dispensed drop falls are the same. The axis and path are only identical when the eye is rotated 90 degrees with respect to the horizon, which can only be easily achieved lying down. Most users dispense eye drops while standing or sitting with the eye rotated about 50 degrees back and will miss often with those types of implementations.

A similar mechanism is described in U.S. Pat. No. 5,932, 206 "Ophthalmic Drug Dispensing System" issued Aug. 3, 1999. The devices disclosed in U.S. Pat. No. 5,932,206 couple a discreet optical gauging mechanism to an eye drop dispenser. By combining the dispensing tip and optical gauging features into a single compact is tip the device becomes more compact, portable, cheaper, and easier to manufacture.

To dispense drugs efficiently with this invention, the user would use a dropper bottle outfitted with the new calibrated tip or would press fit the calibrated tip over the existing tip, tilt his/her head back, position the lens proximal to the eye where drug dispense is desired, align a target with his/her eye until a specified image appears thereby gauging distance, orientation and concentricity with the axis of the eye, then dispense a drop directly into the eye. Since the success rate of delivering a single drop in the desired location, i.e. the eye, will exceed 99%, the amount of waste can be reduced dramatically. At the same time, a visual mechanism by which the dispenser tip is prevented from gaining too close proximity and contacting the eye is provided, thus preventing contamination of the medication and its dispenser.

It is therefore one aspect of the present invention to provide visual feedback from a calibrated optical gauging system embedded in a dropper tip to properly align an ophthalmic drug dispenser to dispense drugs into an eye with a high rate of accuracy.

It is another aspect of the present invention to provide visual feedback from a calibrated optical gauging system embedded in a dropper tip when the ophthalmic drug dispenser becomes too close to the users eye to prevent eye contact and subsequent contamination.

It is another aspect of the present invention to provide a calibrated tip for an eye drop bottle that can be integrated with a bottle of eye drops and is compatible with existing pharmaceutical filling and packaging equipment.

It is another aspect of the present invention to provide a calibrated optical gauging system embedded in a dropper tip as an accessory for aftermarket attachment to any bottle of eye drops.

It is another aspect of the present invention to provide materials compatible with sterilization techniques employed in the pharmaceutical industry.

It is another aspect of this invention to provide promotional advertising to users each time they dispense an eye drop.

It is another aspect of the present invention to provide a means to regulate drop flow and volume.

It is another aspect of the present invention to provide a means to prevent bottles with larger volumes of eye drops from dispensing a drop prior to actuation.

BRIEF DESCRIPTION OF THE DRAWINGS

The present invention will become more fully understood from the detailed description given herein below and the accompanying drawings which are given by way of illustration only, and thus are not limitive of the present invention, and wherein.

DETAILED DESCRIPTION OF THE PREFERRED EMBODIMENTS

Figure 1:
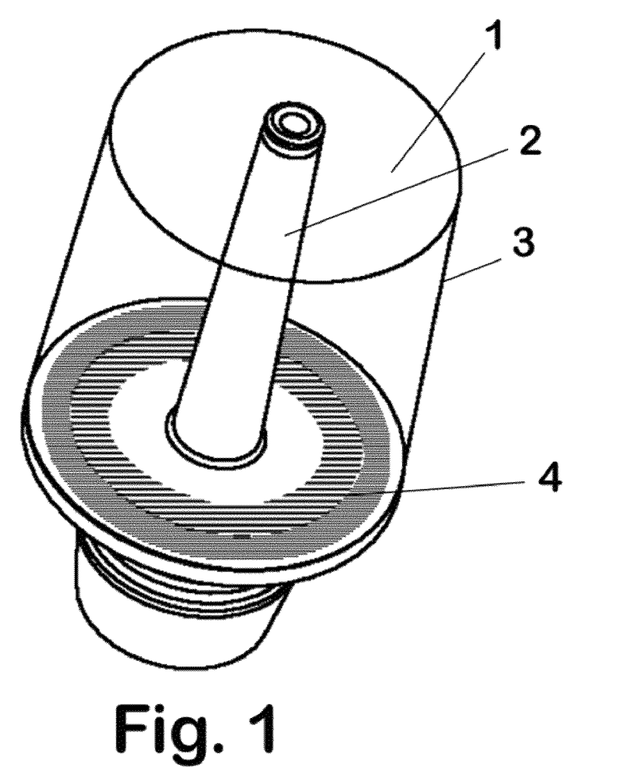
FIG. 1 is perspective view of the preferred embodiment of an optical gauging dispensing tip assembly according to the present invention.

Referring to FIG. 1 an optical gauging dispensing tip assembly 1 in accordance with the present invention is illustrated. The optical gauging dispensing tip assembly 1 is comprised of three main components, a dispensing tip 2 for dispensing an ophthalmic solution, an integrated lens assembly 3 having an integrated housing as will be described below, and an optical target 4 calibrated for use as will be described below. The optical gauging dispensing tip assembly 1 is designed to give visual feedback to dispense an eye drop properly. The eye drop can be any ophthalmic solution comprising either an OTC medication or a prescription medication to treat various eye conditions. To effectively deliver an eye drop, the user needs feedback when the dispensing tip 2 is positioned at the center of the eye and sufficiently close to the eye to guarantee the drop is delivered to the eye. Another requirement is that the dispensing tip 2 does not contact the eye and contaminate the tip with ocular flora, so additional feedback is required as the dispensing tip 2 is brought too close to the eye. The optical target 4 by design gives visual feedback to place the dispensing tip 2 at the center of the eye at a distance from the eye empirically determined to be 0.5 inches (12.7 mm) above the eye. When the dispensing tip is further or closer then 0.5 inches (12.7 mm) from the eye, or off axis, then additional feedback indicates that condition so the user can adjust the position of the dispenser. See FIG. 6 for complete details.

The lens assembly 3 of optical gauging dispensing tip assembly 1 focuses the optical target 4 and has an aperture with a circular field of view. Using the optical target 4 with two concentric rings, inner ring green and outer ring red, the user gets two distinct graphical feedbacks. As the lens assembly 3 approaches the eye, the green ring becomes visible when the eye's axis is vertical and the lens assembly is the optimal distance above the eye to dispense. As the optical gauging dispensing tip assembly 1 becomes too close, the red ring becomes visible, instructing the patient to move the lens assembly further away to avoid contact with the eye.

Figure 2:
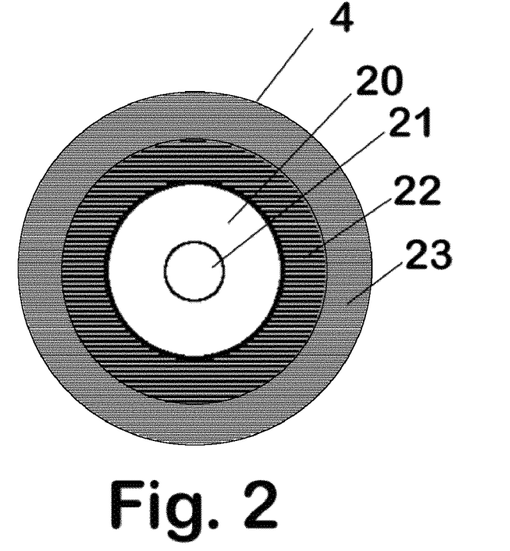
FIG. 2 is a top view of a target that is embedded within the optical gauging dispensing tip assembly according to the invention.

In FIG. 2, the top view of optical target 4 is illustrated. In one embodiment of the present invention, optical target 4 comprises a circular glossy label approximately 0.625 inches (15.8 mm) in diameter. In the center of the label, is a 0.140-inch (3.6 mm) diameter hole 21 that allows the label to maintain an axial and concentric relationship with the nozzle of the tip. The label has an adhesive on its back and is mounted directly on to the surface of the dispensing tip where the base of the nozzle protrudes from the top surface of the tip's base. The label has graphic markings representing important relationships between the distance and location of the dispensing tip and the center of the user's eye. In this embodiment of the present invention there are three rings on the label, a white ring 20, a green ring 22, and a red ring 23. The diameters and thickness of each color ring is calibrated to a range of distances to the user's eye, giving visual feedback to the user that the eye drop dispenser is too far, too close, or in an optimal range to dispense a drop. The rings may be any combination of colors, red and green generally mean stop and go so they were used in this embodiment to provide similar feedback. It will be appreciated that the target can be printed directly on to the tip surface with a printing process such as tampo printing which eliminates the label and its placement.

Figure 3A:
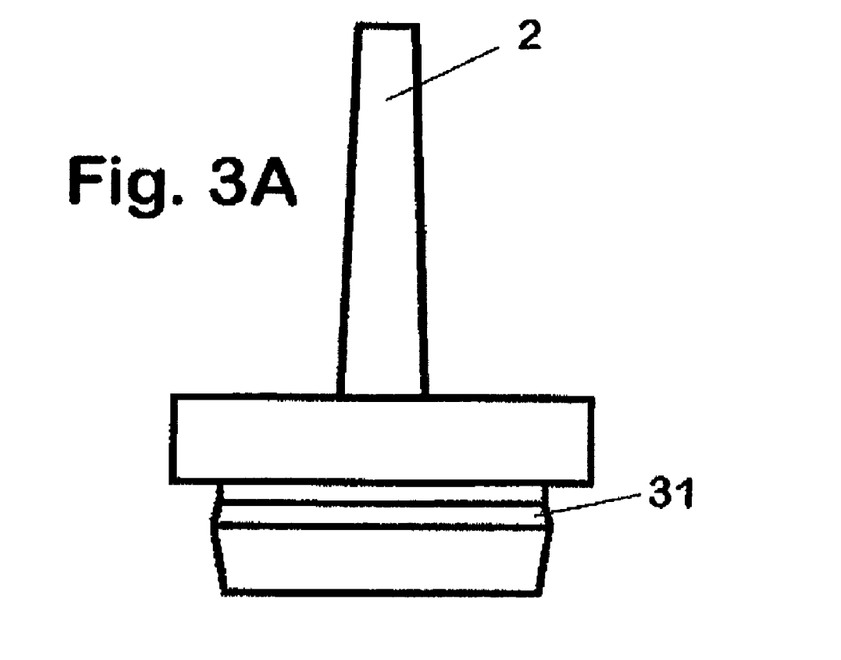
FIG. 3A is a side view and FIG. 3B is a cross-sectional view of a dispensing tip without the optical gauging dispensing tip assembly according to the present invention.
Figure 3B:
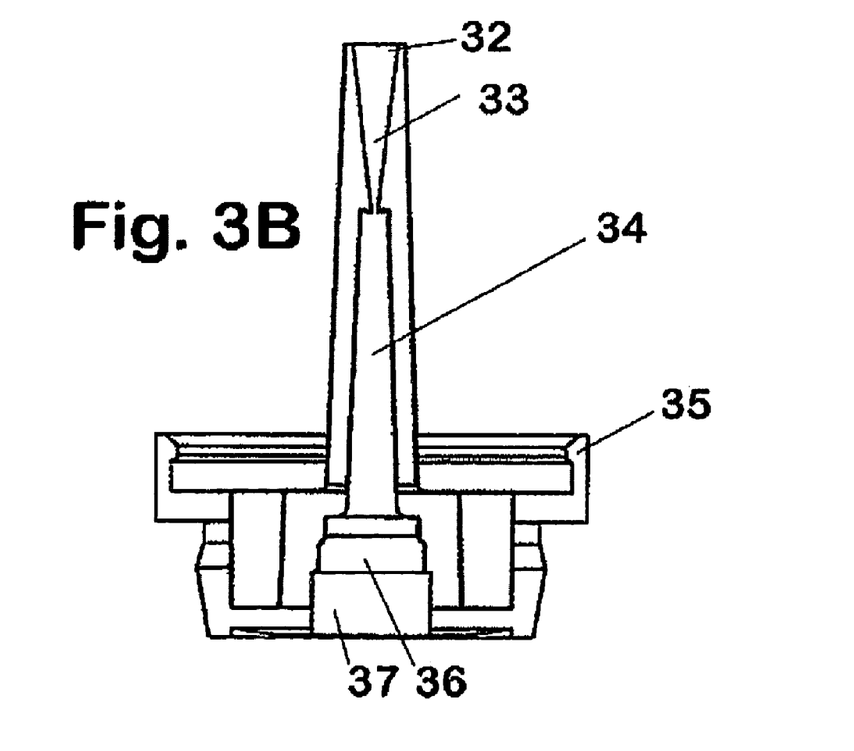

In FIG. 3A, the side view, and in FIG. 3B, a cross-sectional view, of dispensing tip 2 is illustrated. A majority of eye drop bottles and their corresponding tips are molded from plastic resins that are medical grade and capable of being sterilized by e-beam or gamma irradiation, usually a doped polyethylene. The dispensing tip 2 needs to be molded from identical materials and serve the equivalent purpose for all ophthalmic dispensing tips well known in the art that deliver ophthalmic solutions. The dispensing tip 2 conveys the ophthalmic solution from a reservoir in the form of a squeeze bottle through a tube 34 to an orifice 32 designed to dispense a single drop of solution into the eye. The conical section 33 formed within the tube serves two functions. The fluid enters from the inlet side of the conic section through a small resistive orifice and the speed of the fluid decreases as the cross section grows, thereby proving a fluid flow regulating mechanism. This deceleration prevents the fluid from freely streaming out of the orifice 32. The surface area of the walls of the conic section, defines the drop volume by controlling the surface tension with the fluid. Dispensing tips are generally fastened to bottles or reservoirs using an annular ring snap fit, which provides an attachment mechanism for attaching the dispensing tip to the reservoir. The annular ring is embedded in the neck of the bottle and makes a compression fit with an annular groove 31 embedded in the dispensing tip 2. Unfortunately there is no standardization among manufacturers of eye drop bottles for neck size and therefore to make the dispensing tip 2 fit a wide variety of dispensers on the market, an alternative method of attachment includes compression sleeve 37 and compression sleeve 36. Compression sleeve 36 and compression sleeve 37 are designed to press fit over an existing tip instead of replacing it. With different size cross sections, compression sleeve 36 and compression sleeve 37 press fit on to a majority of tips provided on the market. When larger volumes, 1 oz. (30 cc) or greater, of solutions in bottles are inverted to dispense, the solution is held within the confines of the dispenser by a vacuum formed within the bottle. The vacuum needs to exert a force equal to the mass of the solution to prevent leakage. With larger volumes of solutions, the mass of the solution causes some displacement towards the tip before reaching steady state with the vacuum. In dispensers known in the art, the tip does not have a sufficient buffer volume and therefore upon inversion of the bottle, the tip will dispense a drop or two of fluid without activation by squeezing the bottle. The volume of compression sleeve 36 and compression sleeve 37 acts as a buffer for this displacement and prevents the leakage described. Annular ring 35 is molded into the tip to hold the lens assembly on the standard bottle tip and maintain an axial concentric relationship between the lens, target, and tip.

Figure 4:
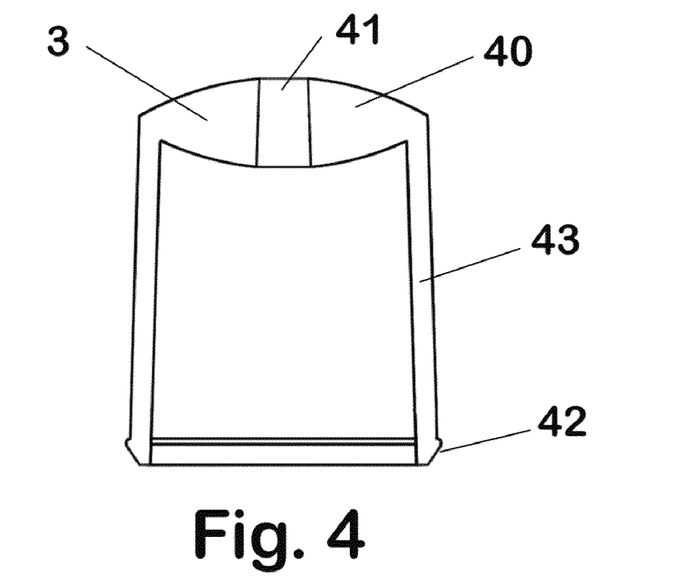
FIG. 4 is a cross-sectional view of the lens for optical gauging dispensing tip assembly with integrated housing according to the present invention.

In FIG. 4, a lens assembly 3 is illustrated. The lens assembly 3 includes a lens 40, which in this embodiment is a biconvex lens. The lens 40 can be spherical or aspherical. The back focal length of the lens 40 is designed to maintain focus of the calibrated optical target as a viewer looks through the lens 40. The equation $1/f=(n-1)*(1/R1-1/R2)$, where f=focal length, n=index of refraction, R1=radius of curvature for first side of the lens, and R2=radius of curvature for second side of the lens, establishes the relationship between the shape of the lens and its focal length. The housing wall 43 establishes the distance between the target and lens and seals the target away from any fluid. The diameter of the lens and its diopter, define the field of view as the lens is moved closer or further from the eye. This relationship establishes a means to provide distance feedback between the eye and dispenser tip. The lens 40 has a hole 41 that is concentric with the lens, thereby providing a mechanism for centering the lens 40 and the dispensing tip. The hole 41 allows the tip to pass through the lens 40 and makes the path the solution takes from the reservoir to the eye isolated from contact with the optical gauging portion of the tip assembly. The tip when nested properly protrudes through the hole about 0.040 inches (1 mm). The lens 40 includes an annular ring 42 to make a hermetic seal with the tip to keep all fluids away from the target label. The lens 40 and its housing 43 are made from optical materials, typically a plastic resin such as doped acrylic that can be sterilized using methods such as e-beam or gamma irradiation or ETO gas and are anti-static.

Figure 5:
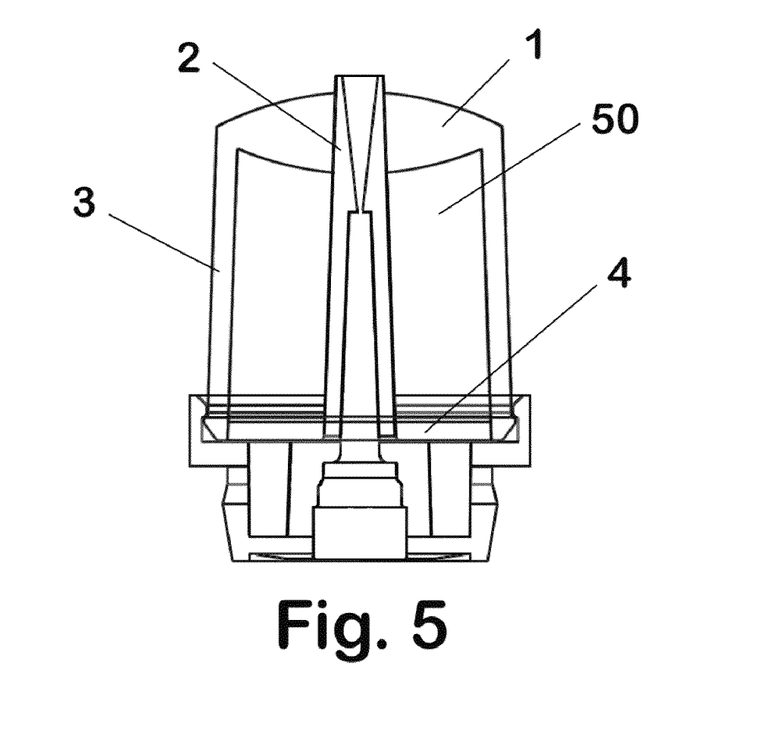
FIG. 5 is a cross-sectional view of the optical gauging dispensing tip assembly, according to the present invention.
Figure 6A:
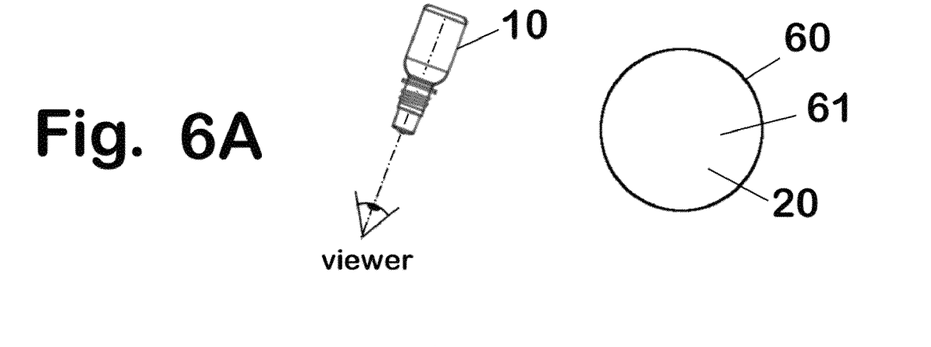
FIGS. 6A, 6B, 6C and 6D illustrate the relationship between the orientation of the optical gauging dispensing tip assembly and a viewer, according to the present invention.
Figure 6B:
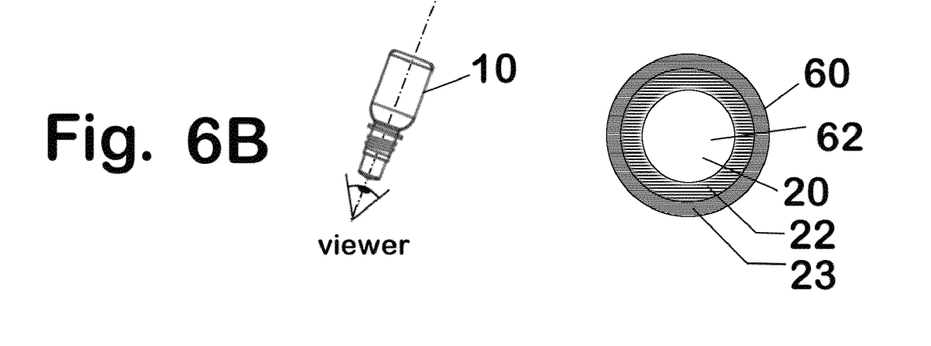
Figure 6C:
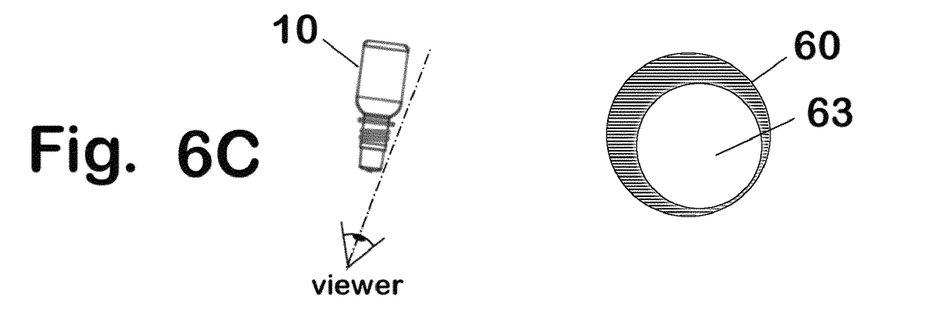
Figure 6D:
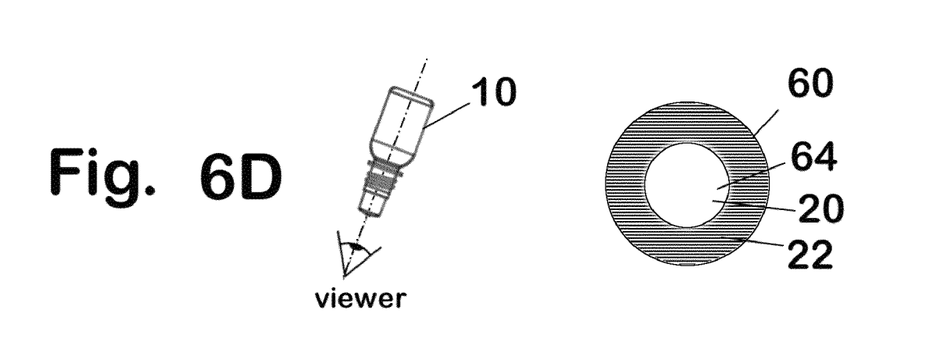

FIG. 5 is a cross-sectional view of the assembled optical gauging dispensing tip assembly 1. Once assembled, inner chamber 50 containing optical target 4 is hermetically sealed with the annular ring seal at the base of the lens and the tip press fit into the hole through the lens. The combination of the dispensing tip 2 press fit through the hole 41 and the annular ring 42 at the base mechanically maintains an axial concentric relationship between the lens 40, optical target 4, and dispensing tip 2.

Figure 11A:
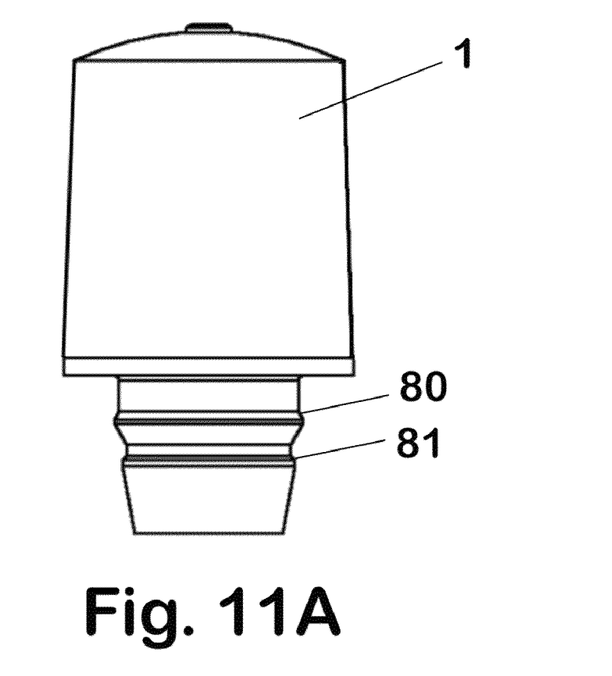
FIG. 11A is side view of another embodiment of the optical gauging dispensing tip assembly, according to the present invention.
Figure 11B:
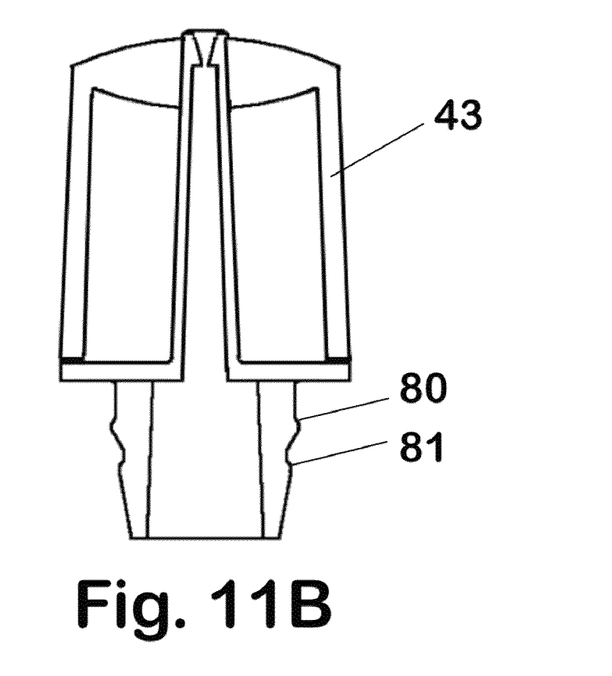
FIG. 11B is a cross-sectional view of the other embodiment of the optical gauging dispensing tip assembly, according to the present invention.
Figure 12:
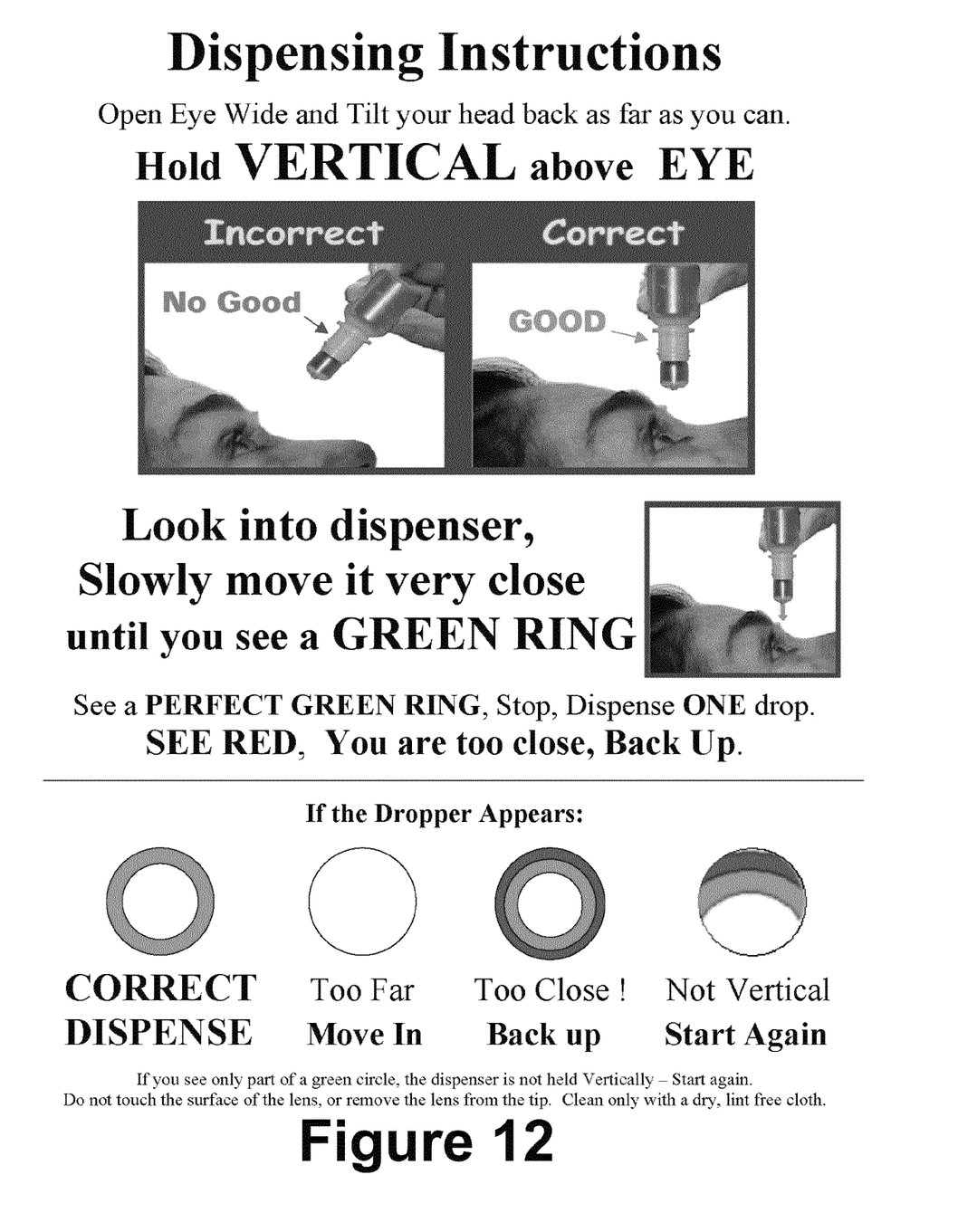
FIG. 12 Dispensing Instructions reference

FIGS. 6A, 6B, 6C, and 6D illustrate the effect on image 60 as eye drop dispensing assembly 10 is moved along the optical axis of the viewer as illustrated. The resulting image gives the user feedback on where to hold eye drop dispensing is assembly 10 to properly dispense a drop into the eye. Image 60 is the image the user sees when looking into the optical gauging assembly that is integral to eye drop dispensing assembly 10. The assembly 10 is held in a near vertical orientation above the eye, with the dispensing orifice proximal to the eye. The user looks into the lens to view a target. The viewing target within eye drop dispensing assembly 10 is the same as illustrated in FIG. 2 containing three color regions, a white inner circle, followed by a concentric green ring, with an outer concentric red ring. In FIG. 11A there is a range of distances from the viewer where the optical gauging assembly yields pattern 61 on image 60 as illustrated. The pattern 61 of image 60 reveals pure white circle 20, which indicates the eye drop dispensing assembly 10 is too far to dispense a drop properly. The pattern 61 would provide feedback to move the eye drop dispensing assembly 10 closer to the eye. In FIG. 11B there is a range of distances from the viewer where the optical gauging assembly yields pattern 62 on image 60 as illustrated. The pattern 62 of image 60 reveals an outer red ring 23, central green ring 22, and a white inner region 20, which indicates the eye drop dispensing assembly 10 is too close to the user and they are in danger of making contact with their eye. The pattern 62 would provide feedback to move the eye drop dispensing assembly 10 away from the eye. In FIG. 11C the eye drop dispensing assembly 10 is not located on the optical axis of the viewer where the optical gauging assembly yields pattern 63 on image 60 as illustrated. The pattern 63 of image 60 reveals non-concentric patterns of rings, which indicates the eye drop dispensing assembly 10 is off of the optical axis of the eye. The pattern 63 would provide feedback to rotate or offset the eye drop dispensing assembly 10 back on to the optical axis of the eye. In FIG. 11D there is a range of distances from the viewer where the optical gauging assembly yields pattern 64 on image 60 as illustrated. The pattern 64 of image 60 reveals an outer green ring 22, and a white inner region 20, which indicates the eye drop dispensing assembly 10, is in the perfect relation to the eye to dispense a drop. The pattern 64 would provide feedback to dispense a drop. The range of distances discussed above and the resulting images 60 are repeatable independent of viewer. The distance can be calibrated by varying the pattern, lens diameter, or optics and the combination of these three parameters can is be determined empirically to achieve the feedback desired. Therefore eye drop dispensing assembly 10 can be calibrated to have a user position it directly along the center of the viewer's optical axis at a specific distance to dispense a drop.

Figure 7A:
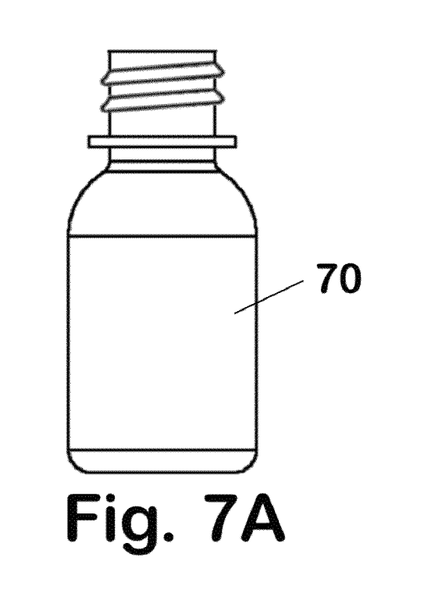
FIG. 7A is a side view of a typical ophthalmic solution bottle.
Figure 7B:
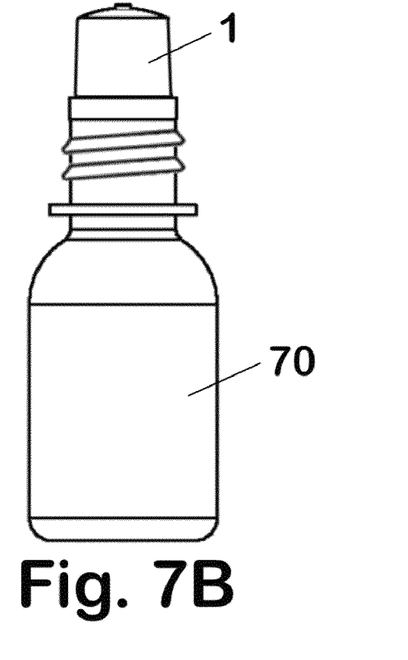
FIG. 7B is side view of the optical gauging dispensing tip assembly attached to the ophthalmic solution bottle according to the present invention.

In FIGS. 7A and 7B, a typical dispensing bottle for ophthalmic solutions is shown. Optical gauging dispensing tip assembly 1, is inserted into the neck of the dispensing bottle where its annular groove feature 31, illustrated in FIGS. 3A and 3B, engage with annular ring features in the neck of the dispensing bottle. In a typical automated filing line for eye drops, the line is configured to feed empty bottles down a conveyor to a filing tube. The tube dispenses solution into the bottle, and the filled bottle is conveyed to a tip insertion station. The tips are bowl fed to an actuator that press fits the tips into the bottle. The filled bottle with tips is conveyed to a capping station, where caps are threaded over the tip on to the neck of the bottle. The integrated optical gauging dispensing tip assembly 1 in this embodiment allows filing ophthalmic solution bottles on the same production equipment in the same three steps. This eye drop dispensing assembly 10 is one embodiment for the present invention.

Figure 8A:
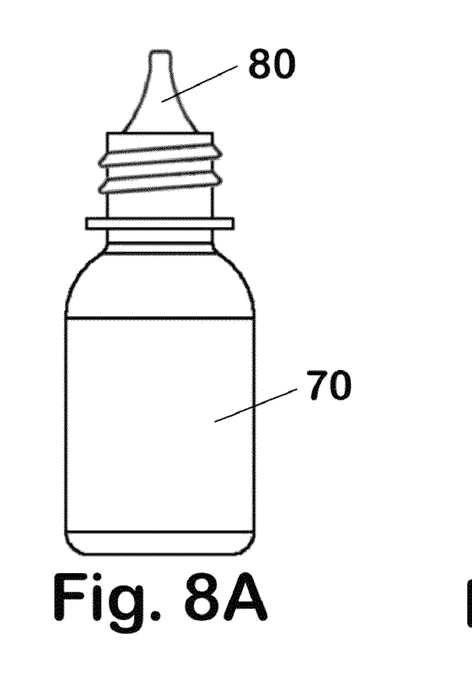
FIG. 8A is a side view of a typical ophthalmic solution bottle with typical dispensing tip attached.
Figure 8B:
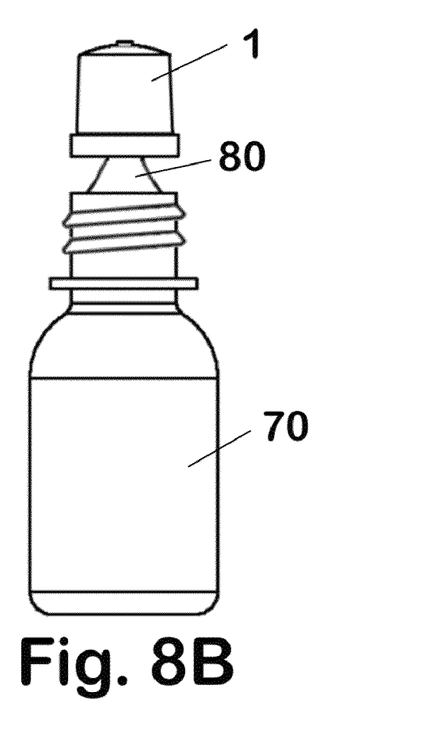
FIG. 8B is side view of the optical gauging dispensing tip assembly attached to the tip of the ophthalmic solution bottle according to the present invention.

In FIGS. 8A and 8B, a typical dispensing bottle with a typical dispensing tip for ophthalmic solutions is shown. Optical gauging dispensing tip assembly 1, is inserted on to tip 80 of the dispensing bottle where compression sleeve 36 and compression sleeve 37, illustrated in FIG. 3B, engage with a compression fit around the surface of the tip 80. It will be appreciated that such dispensing tips can have different profiles, cross-sections, can be taller or shorter, and generally vary from one supplier to another. The soft nature of polyethylene allows compression sleeve 36 and compression sleeve 37 to form and seal around a majority of these dispensing tips.

Figure 9A:
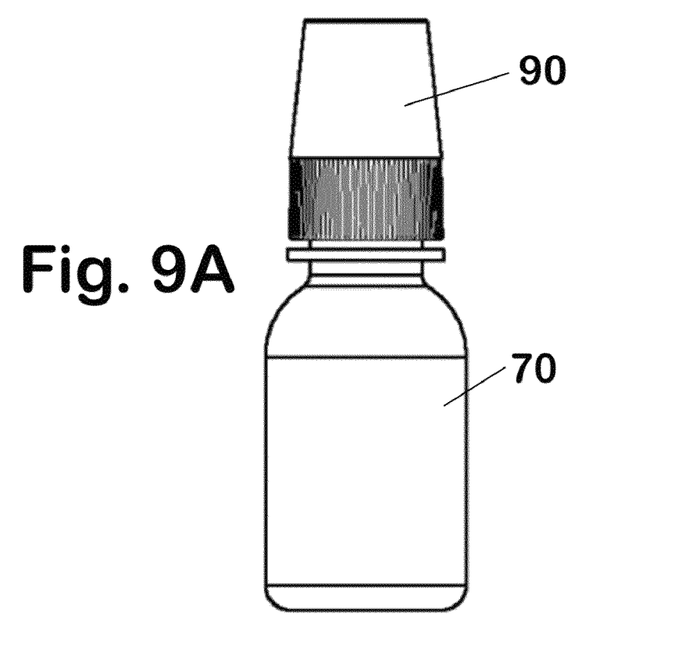
FIGS. 9A and 9B are side views of the optical gauging dispensing tip assembly attached to the ophthalmic solution bottle with caps according to the present invention.

In FIG. 9A, the assembly illustrated in FIG. 7B is capped to seal off the tip of the dispensing bottle. The cap 90 provides a closure mechanism that needs to maintain a hermetic seal for the tip and in this embodiment of the present invention is internally threaded to screw on to the threads of the neck of bottle 70. The cap 90 is made from materials, typically a plastic resin such as polypropylene that can be is sterilized using methods such as e-beam or gamma irradiation or ETO gas.

Figure 9B:
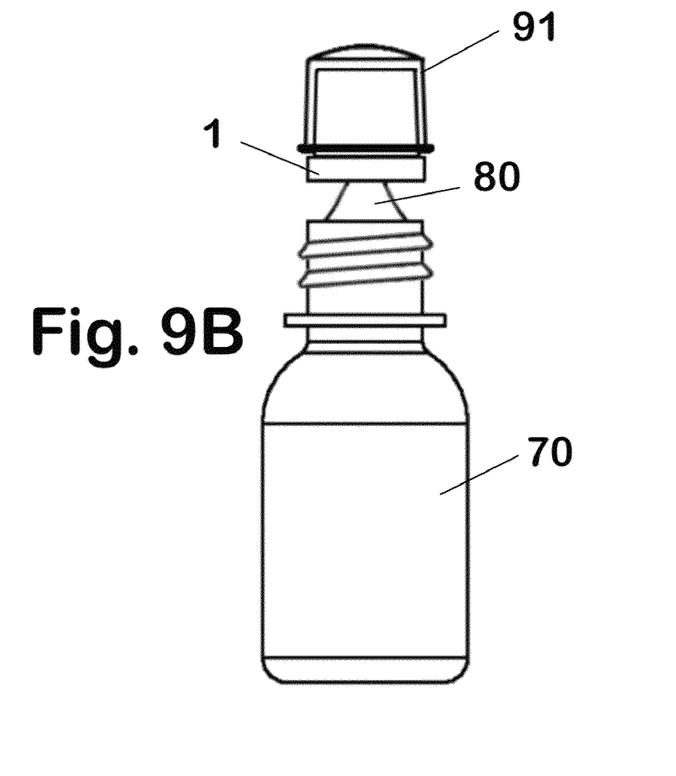
Figure 10A:
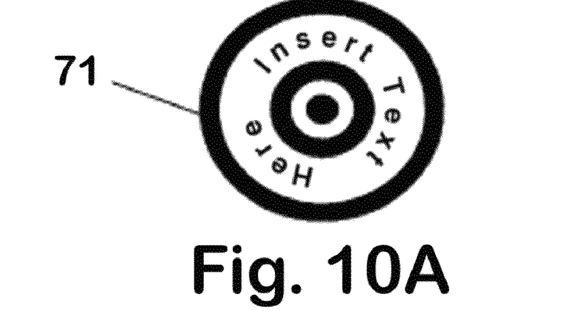
FIGS. 10A, 10B, 10C and 10D are top views of optical targets for the optical gauging assembly, according to the present invention.
Figure 10B:
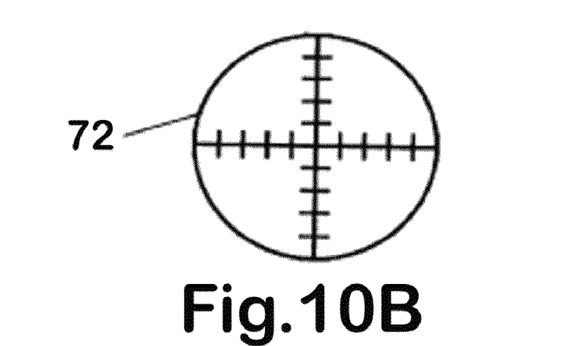
Figure 10C:
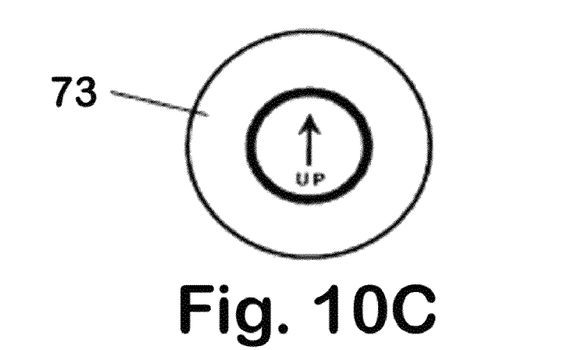
Figure 10D:
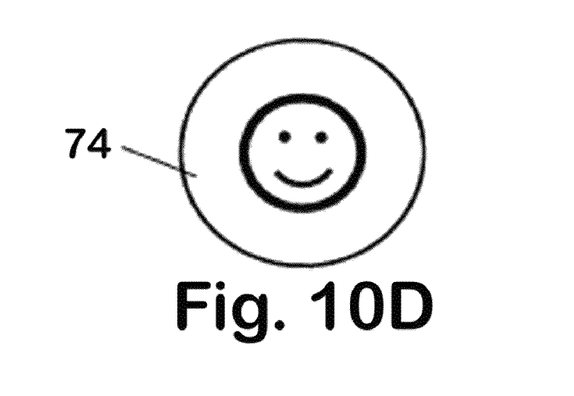

In FIG. 9B, the assembly illustrated in FIG. 8B is capped to seal off the tip of the dispensing bottle. The cap 91 provides a closure mechanism that needs to maintain a hermetic seal for the tip and in this embodiment of the present invention is press fit on to the lens of optical gauging dispensing tip assembly 1. The cap 91 is made from materials, typically a plastic resin such as polypropylene that can be sterilized using methods such as e-beam or gamma irradiation or ETO gas.

FIGS. 10A, 10B, 100, 10D illustrates the various patterns that can be printed and used as optical targets for the purpose of positioning optical gauging dispensing tip assembly 1 along the center of a viewers optical axis at a specific distance. To calibrate a fixed distance from a viewer, optical target 71 would specify which ring of the concentric ring pattern to align with the outer diameter of the image field of view. Optical target 71 further includes a text message, such as "Dispense now" or "Try new product A". The text message could indicate the dispenser's use, or could advertise a product or company every time the user dispenses drops. To calibrate a fixed distance from a viewer, optical target 72 would specify which vertical and horizontal hash mark to align with the outer diameter of the image field of view. To calibrate a fixed distance from a viewer, optical target 73 will align the ring with the outer diameter of the image field of view and the arrow will indicate a preferred orientation such as up. To calibrate a fixed distance from a viewer, optical target 74 will align the ring with the outer diameter of the image field of view and the graphic would specify a preferred orientation such as up. It should be apparent that the optical target pattern can be graphically calibrated, color calibrated, or use text instructions or advertising printed within the optical target pattern to accomplish the same purpose.

In FIG. 11A, a side view, and in FIG. 11B, a cross-sectional view, of optical gauging dispensing tip assembly 1 is illustrated. This embodiment of the present invention incorporates annular groove 80 and annular groove 81. Having progressively larger annular grove diameters allows the optical gauging dispensing tip assembly 1 to fit into multiple off the shelf dispensing bottles with different neck sizes.

It will thus be seen that the objects set forth above, and those made apparent from the preceding descriptions, are effectively attained and since certain changes may be made in the above construction without departing from the spirit and scope of the invention, it is intended that all matter contained in the above description or shown in the accompanying drawings, shall be interpreted as illustrative and not in a limiting sense.

It is also to be understood that the following claims are intended to cover all generic and specific features of the invention herein described and all statements of scope of the invention, which as a matter of language, might be said to fall therebetween.

What is claimed is:

1. An apparatus that when attached to a reservoir of ophthalmic solutions or drugs optically guides the user to position both the eye and dispenser in a three dimensional spatial alignment that enables an ophthalmic drop dispensed and falling along its gravitational path to enter the eye for users that are standing, sitting, or lying on their back while dispensing ophthalmic solutions and drugs, the apparatus comprising:

a passageway through a dispensing tip supplying and contacting the ophthalmic solutions and drugs to a dispensing orifice in droplet form;

said passageway additionally includes a mechanism to regulate solution flow and dispense a given drop volume;

said dispensing tip protrudes through a sealed optical gauging device that isolates the fluid path from the optical gauging components;

said optical gauging device comprises a plastic or glass lens with a fixed aperture formed integrally with protruding walls to form a sealed chamber that is mechanically coupled in axial alignment at the correct focal distance from precision symmetrical graphical markings;

the said markings become visible as the optical gauging device becomes proximal to the eye;

the said markings are constructed such that the inclusion of said markings only occur at precise calibrated distances from the eye;

as said markings become visible, symmetry of the said markings are indicative that optical gauge is in axial alignment with the optical axis of the eye;

as said assembly is located in vertical alignment, vertically above the user's eye prior to dispense, movement of the eye along with movement of the said assembly in response to graphical feedback combine to create a vertical axial alignment with the optical axis of a user's eye at a set distance between said optical gauging device and the user's eye to position said dispensing orifice in a 3D spatial alignment for delivering ophthalmic solutions and drugs to the user's eye;

said dispensing tip and optical gauging device combined in an integral sub-assembly with an attachment mechanism comprised of at least one of an external compression fit sleeve, internal compression fit sleeve, external thread, internal thread, or base for ultrasonic weld to secure said assembly to a reservoir of ophthalmic solutions and drugs; and a closure mechanism to seal said dispensing orifice.

2. The apparatus according to claim 1, wherein said optical gauging device includes a printed viewing target having a design marked thereon.

3. The apparatus according to claim 2, wherein said optical gauging device includes at least one lens disposed axially with said target at a focal distance to clearly view said viewing target.

4. The apparatus according to claim 3, wherein said at least one lens is a double convex aspherical magnifying lens having a fixed diameter, diopter, and field of view.

5. The apparatus according to claim 4, further comprising a cylindrical wall molded integrally with said double convex magnifying lens, said wall and lens forming a chamber where the height of the chamber is the focal length of the said double convex magnifying lens, and said viewing target, to maintain axial and concentric alignment between said double convex magnifying lens and said viewing target.

6. The apparatus according to claim 1, wherein said attachment mechanism includes at least one external annular groove used to attach said dispensing tip to said reservoir said reservoir including a mating annular ring.

7. The apparatus according to claim 2, wherein said viewing target design includes an inner circle of a first color, a central ring of second color, and an outer ring of a third color all disposed concentrically with said inner circle where said first color, said second color, and said third color only become visible within the visual field of the lens of said optical gauging device as the lens becomes sufficiently close to the eye and are indicative of distances between said dispensing tip and a user's eye.

8. The apparatus according to claim 7, wherein the diameter, focal length, and magnification of said double convex magnifying lens and diameters of said circles on said target, are selected to provide an axial relationship to a users eye and gauge the distance from the users eye to the dispensing tip where said gauged distance is segregated into regions indicative of when dispensing tip is too close, too far, or in an optimal range to dispense a drop into the eye and where said circles on said target are not visible in their entirety when a non-axial alignment exists between the user's eye and the said dispensing tip.

9. The apparatus according to claim 2, wherein said viewing target design includes at least one circle and textual information.

10. The apparatus according to claim 1, wherein said attachment mechanism includes at least two external annular grooves used to attach said dispensing tip to said reservoir, said reservoir including a mating annular ring.

11. The apparatus according to claim 1, wherein said attachment mechanism includes a recessed sleeve at the inlet of said dispensing tip that is used to press fit said dispensing tip axially on to an existing dispensing tip of an ophthalmic solution reservoir.

12. The apparatus according to claim 11, wherein said recessed sleeve has multiple cross-section diameters to press fit on to a range of said existing dispensing tip shapes and sizes.

13. The apparatus according to claim 1, wherein said regulating mechanism includes a conical geometry within said passageway of said dispensing tip with a small inlet proximal to said reservoir and large outlet forming said dispensing orifice.

14. The apparatus according to claim 1, wherein said dispensing tip, optical gauging device, and closure mechanism are fabricated using plastic resins, paper, and ink capable of withstanding at least one means of microbial sterilization.

15. The apparatus according to claim 5, wherein said dispensing tin protrudes through a concentric hole in said double convex magnifying lens with minimal clearance to deliver ophthalmic solution without incidental contact with any component of said optical gauging device.

16. The apparatus according to claim 5, wherein said closure mechanism includes at least one closure comprising a plastic cap attached to said double convex magnifying lens or a threaded plastic cap that threads on to the neck of said reservoir.

17. The apparatus according to claim 5, wherein said closure mechanism includes at least one closure comprising a plastic cap that threads on to the neck of said reservoir.

18. The apparatus according to claim 1, wherein said dispensing tip, optical gauging device, and closure mechanism are fabricated of materials doped or coated with anti-static compounds.

19. A method of dispensing ophthalmic solutions to an eye, comprising:

providing a container having a dispensing tip at one end and a passageway from the container through the tip to a dispensing orifice, in which the container is adapted for dispensing at least one droplet from the orifice of the tip;

press fit an optical gauging dispensing tip assembly on to said tip providing a hermetic seal in axial alignment to the dispensing tip of the container to create a contiguous passageway from the container through the dispensing tip, and through optical gauging dispensing tip to a dispensing orifice for dispensing at least one droplet from the orifice of the dispensing tip;

tilting head back;

aligning the container with the optical gauging dispensing tip vertically above the eye, the dispensing orifice proximal to the eye, forcing the optical axis of the eye into vertical alignment when the user looks into a lens integral with the optical gauging dispensing tip and observing a target indicator looking for a least one concentric graphical image indicating vertical axial alignment between the optical gauging dispensing tip and the eye;

gauging distance from the eye by moving container with optical gauging dispensing tip up and down along eyes optical axis while looking through lens on optical gauging dispensing tip and responding to graphical images indicating one of three conditions, too far from the eye to dispense a drop effectively, too close to the eye-avoid contact with the eye to avoid tip contamination, and perfect distance from the eye to deliver a drop;

dispensing the liquid from the container into the eye of the user by actuating the container to dispense a drop from the orifice of the tip while holding container with optical gauging dispensing tip along the optical axis of the eye at an exact predetermined distance to effectively dispense a drop into the eye without making contact with the eye.

20. The apparatus according to claim 19, wherein said viewing target design includes an inner circle of a first color, a central ring of second color, and an outer ring of a third color all disposed concentrically with said inner circle where said first color, said second color, and said third color are indicative of distances between said dispensing tip and a user's eye.

* * * * *